(12) United States Patent
Stamper et al.

(10) Patent No.: US 7,592,173 B1
(45) Date of Patent: Sep. 22, 2009

(54) OPERATIONALLY ENHANCED BIOREACTOR

(75) Inventors: David M. Stamper, Clarksburg, MD (US); Marianne Walch, Millsboro, DE (US); Darrell H. Hill, Monroeville, NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 758 days.

(21) Appl. No.: 10/826,789

(22) Filed: Apr. 16, 2004

Related U.S. Application Data

(60) Provisional application No. 60/465,231, filed on Apr. 25, 2003.

(51) Int. Cl.
*C12M 1/14* (2006.01)
*C12M 3/04* (2006.01)
(52) U.S. Cl. .................................. 435/299.1; 435/298.1
(58) Field of Classification Search .............. 435/299.1, 435/289.1; 422/129, 130
See application file for complete search history.

(56) References Cited

U.S. PATENT DOCUMENTS

| | | | | |
|---|---|---|---|---|
| 3,198,005 | A * | 8/1965 | Wolfson | 73/61.62 |
| 4,561,815 | A * | 12/1985 | Trevarrow | 409/227 |
| 5,081,036 | A * | 1/1992 | Familletti | 435/296.1 |
| 5,641,642 | A * | 6/1997 | Peyton et al. | 435/9 |
| 6,432,698 | B1 * | 8/2002 | Gaugler et al. | 435/296.1 |
| 2003/0153059 | A1 * | 8/2003 | Pilkington et al. | 435/161 |

* cited by examiner

*Primary Examiner*—Jill Warden
*Assistant Examiner*—Shanta G Doe
(74) *Attorney, Agent, or Firm*—Jacob Shuster; Dave A. Ghatt

(57) ABSTRACT

Biofilm on glass beads deposited within a bottom portion of a vertically elongated bioreactor housing for possible experimental evaluation through a testing port in the housing which is also provided with inlet ports for aeration and infeed of nutrients with liquid. The biofilm collected within the housing chamber undergoes growth on glass slides within a cross-sectionally rectangular portion of the bioreactor housing from which the slides may be upwardly withdrawn under selective control without biofilm damage. The bioreactor housing arrangement also provides a high length to width ratio designed to enhance aeration.

7 Claims, 2 Drawing Sheets

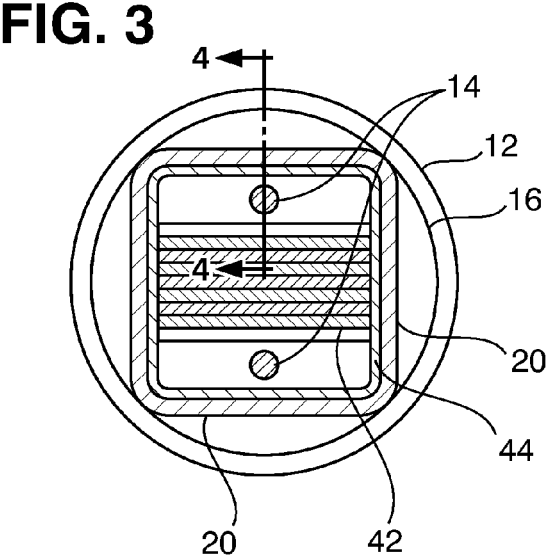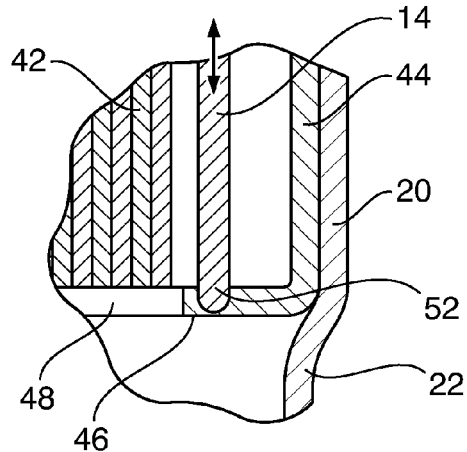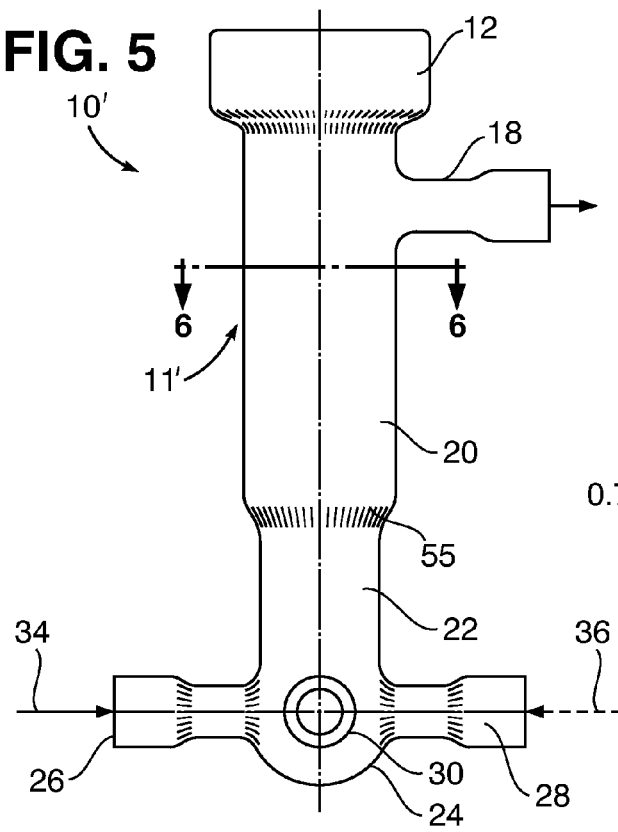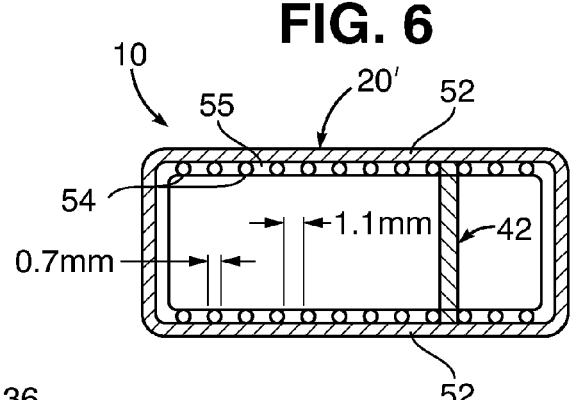

OPERATIONALLY ENHANCED BIOREACTOR

CROSS-REFERENCE TO RELATED APPLICATION

This application claims the benefit of U.S. Provisional Application No. 60/465,231 filed Apr. 25, 2003, entitled "OPERATIONALLY ENHANCED BIOREACTOR", incorporated herein by reference.

STATEMENT OF GOVERNMENT INTEREST

The invention described herein may be manufactured and used by or for the Government of the United States of America for governmental purposes without the payment of any royalties thereon or therefore.

The present invention relates generally to bioreactors through which evaluation of biofilms is enhanced.

BACKGROUND OF THE INVENTION

The structural and functional condition of biofilms is presently studied and evaluated by use of experimental laboratory devices such as bioreactors as generally known in the art. Such bioreactors induce growth of biofilm therein on glass microscope slides from which the biofilm is collected on glass beads subject to aeration within a testing chamber for experimental evaluation purposes. However, various problems heretofore arose with respect to such use of bioreactors involving poor aeration during the biofilm growth process and difficulty in selective removal of microscope slides without disruption of biofilm growth on the slides and collection thereof on the glass beads.

SUMMARY OF THE INVENTION

Pursuant to the present invention the housing of a bioreactor has several ports for aeration of biofilm coated glass beads deposited therewithin, to supply nutrients and liquid thereto, and to allow outflow from the housing chamber. Microscope slides on which biofilm growth occurs are located within the bioreactor housing from which a microscope side is slidably withdrawn from the open end of the bioreactor housing by removing a holder holding the slide or by forceps to avoid biofilm disruption caused by withdrawal. A relatively high length to width dimensional ratio for the bioreactor housing is provided, such as 7:1, so as to ensure complete aeration within the bioreactor housing chamber during biofilm growth.

BRIEF DESCRIPTION OF DRAWING

A more complete appreciation of the invention and many of its attendant advantages will be readily appreciated as the same becomes better understood by reference to the following detailed description when considered in connection with the accompanying drawing wherein:

FIG. 3 is a traverse section view taken substantially through a plane indicated by section line 3-3 in FIG. 2;

FIG. 4 is a partial section view taken substantially through a plane indicated by section line 4-4 in FIG. 3;

FIG. 5 is a side elevation view of another embodiment of the present invention with respect to the biofilm testing bioreactor; and FIG. 6 is a transverse section view taken substantially through a plane indicated by section line 6-6 in FIG. 5.

DETAILED DESCRIPTION OF PREFERRED EMBODIMENT

Figure 1:
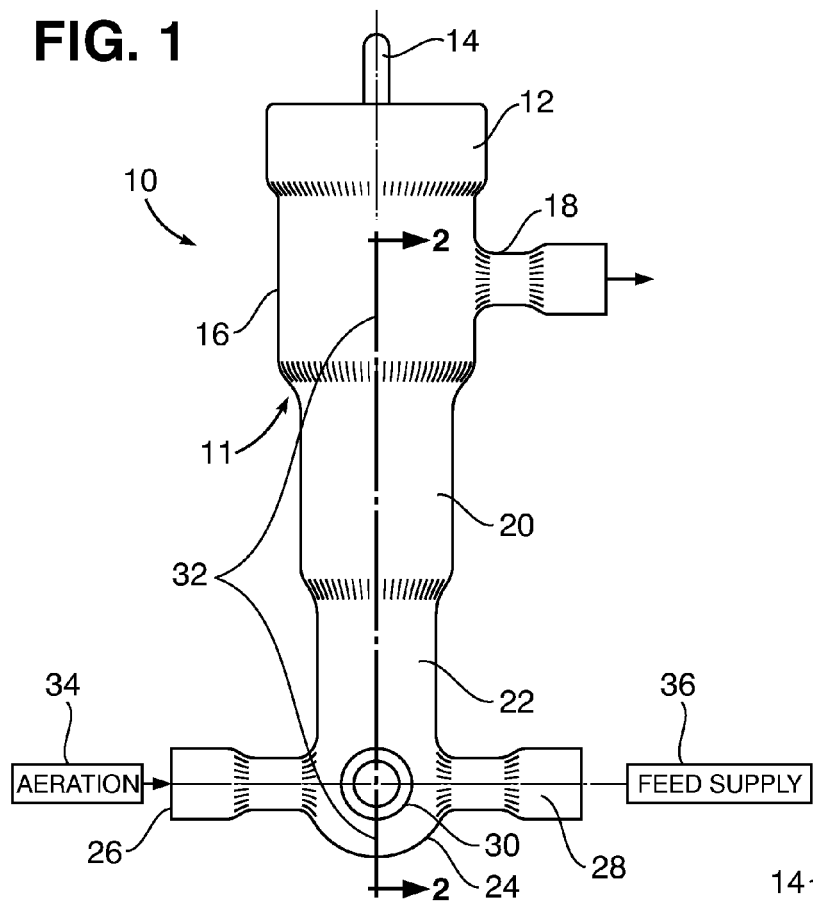
FIG. 1 is a side elevation view of a biofilm testing bioreactor, in accordance with one embodiment of the present invention.
Figure 2:
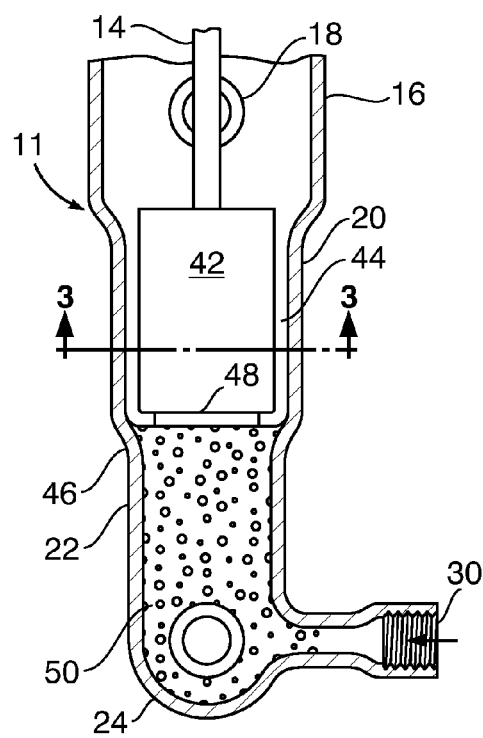
FIG. 2 is an enlarged partial section view taken substantially through a plane indicated by section line 2-2 is in FIG. 1.

Referring now to the drawing in detail, FIGS. 1 and 2 illustrate a bioreactor 10 having a vertically elongated housing 11 which includes an upper sealable top end portion 12 from which insertable retraction rods, actuating means, 14 may project. An upper housing section 16 of the housing 11 which can be of a smaller diameter than the top end portion 12 extends downwardly therefrom. The upper housing section 16 has an outlet port 18 connected thereto. From the upper housing section 16, a cross-sectionally mid-housing section 20 further extends downwardly to a lower housing section 22 of smaller diameter, closed at its bottom end to form a testing chamber 24 within the bioreactor housing 11 having internally threaded inlet ports 26, 28 and 30. Aeration inflow 34 and nutrient infeed supply 36 to the testing chamber 24 of the housing are respectively delivered thereto through the ports 26 and 30 as shown in FIG. 1.

As shown in FIGS. 2, 3 and 4, a plurality of glass slides 42 are positioned in the mid-housing section 20 above the lower housing section 22 by retention within a holder 44 having a bottom 46 within which an opening 48 is formed, through which upflow of feed fluid and aeration is conducted between the slides 42 from the lower housing section 22 and testing chamber within which glass beads 50 are deposited to fill the lower housing section 22, up to the lower portion of the mid-housing section 20.

The slide holder 44 with the slides 42 therein may be retracted upwardly from the mid-housing section 20 for removal from the bioreactor 10 through its top end portion 12 by means of the rod(s) 14. At least one rod 14, metal, plastic, glass or the like, is accordingly provided with a threaded end 52, threadedly inserted into the bottom 46 of the holder 44 as shown in FIG. 4.

It will be apparent from the foregoing description, that beneficial location of the aeration inlet port, the feed supply port, and the possible testing port 26, 28, 30 to the testing chamber portion 24 of the bioreactor housing 11 enhances aeration fluid flow and testing. Also, removal and replacement of the slides 42 is enhanced by the holder 44 with the rod(s) 14 connected thereto, in an arrangement which accommodates a housing configuration providing a large length to width ratio of 10:1 to 5:1, preferably 7:1, in order to achieve increased aeration. Furthermore, the bioreactor arrangement as previously described provides for a relatively high ratio (above 10 square centimeters per milliliter) for internal surface area in the housing chamber 32 on the slides 42 and the beads 50, to the volume of the infeed liquid being processed. Housing chamber 32 includes 24, 22, 20 and up-to outlet port 18 of 16.

Referring now to FIGS. 5 and 6, a bioreactor 10' in accordance with another embodiment of the present invention is illustrated. The bioreactor 10' has a vertically elongated housing 11' which includes the aforementioned lower housing section 22 with the closed testing chamber 24 and the three ports 26, 28 and 30. The rest of the housing 11' is formed by a cross-sectionally contoured mid-housing section 20' extending from the lower housing section 22 to the upper sealable top end portion 12 just above the outlet port 18. The mid-housing section 20' has fixedly mounted on opposite sides walls 52 thereof adjacent the lower section 22 a plurality of closely spaced guide rods 54 above a neck 55 between the housing sections 20' and 22 as shown in FIG. 6. The aforementioned glass slides 42 are accordingly manually positioned and removed from within the mid-housing section 20' above the collection of deposited beads 50 in the lower housing section 22 between the guide rods 54 by insertion into the housing 11' through the open end of the sealable top portion 12, using tweezers (not shown). As shown in FIG. 6, the guide rods have a diameter of about 0.7 mm. FIG. 6 also shows the distance between the closely spaced guide rods to be about 1.1 mm.

Obviously, other modifications and variations of the present invention may be possible in light of the foregoing teachings. It is therefore to be understood that within the scope of the appended claims the invention may be practiced otherwise than as specifically described.

What is claimed is:

1. A bioreactor arrangement comprising:
    an axially elongated housing comprising:
        a top housing section having one or more diameters;
        a middle neck portion having a funnel shape;
        a mid-housing section extending below the top housing section and having a rectangular cross section, wherein the mid-housing section is attached to the top housing section via the middle neck portion;
        a lower neck portion having a funnel shape;
        a cylindrical lower housing section extending below the mid-housing section and attached to the mid-housing section via the lower neck portion, the cylindrical lower housing having a third diameter smaller than the one or more diameters, the cylindrical lower housing closed at a bottom end forming a testing chamber, the cylindrical lower housing having glass beads therein; and
    one or more slides for holding biofilm growth positioned within the mid-housing section.

2. The bioreactor arrangement of claim 1, wherein the mid-housing section includes,
    two oppositely positioned side walls,
    a plurality of closely spaced guide rods inning upwardly along each of the two oppositely positioned side walls, the spaced guide rods positioned above the lower neck portion, with adjacent guide rods along each of the two oppositely positioned side walls forming grooves through which the one or more slides may be slid, and wherein the grooves and the lower neck portion support the one or more slides in an upright position within the mid housing section.

3. The bioreactor arrangement of claim 2, further comprising:
    an aeration inlet port located at the testing chamber;
    a feed supply inlet port located at the testing chamber;
    a testing inlet port located at the testing chamber; and
    an outlet port located at the mid-housing section.

4. The bioreactor arrangement of claim 2, wherein each of the plurality of guide rods has a diameter of about 0.7 mm and wherein the distance between the closely spaced guide rods is about 1.1 mm.

5. The bioreactor arrangement of claim 1, wherein the top housing section comprises:
    a cylindrical sealable top portion having a first diameter;
    an upper neck portion having a funnel-like shape;
    a cylindrical upper housing portion extending below the cylindrical sealable top portion and attached to the cylindrical sealable top portion via the upper neck portion, the cylindrical upper housing portion having a second diameter smaller than the first diameter; the bioreactor arrangement further comprising a rectangular holder removeably positioned within the mid-housing section of the elongated housing for retaining said one or more slides, the rectangular holder having outer walls that contact walls of the mid-housing section, the rectangular holder supported on the lower neck portion which prevents the holder from sliding down into the testing chamber.

6. The bioreactor arrangement of claim 5, wherein the rectangular holder comprises:
    a bottom portion with a threaded opening, and the at least one actuator comprises a rod having a threaded end, wherein the threaded end of the rod is threadedly inserted into the threaded opening in the bottom portion of the rectangular holder; and
    a second opening at the bottom portion through which fluids from the underlying cylindrical lower housing section flows.

7. The bioreactor arrangement of claim 6, further comprising:
    an aeration inlet port located at the testing chamber;
    a feed supply inlet port located at the testing chamber;
    a testing inlet port located at the testing chamber; and
    an outlet port located at the cylindrical upper housing portion.

* * * * *